United States Patent [19]
Tice et al.

[11] Patent Number: 5,736,928
[45] Date of Patent: Apr. 7, 1998

[54] PRE-PROCESSOR APPARATUS AND METHOD

[75] Inventors: Lee D. Tice, Bartlett; Frank Kuzhiyil, Glendale Heights, both of Ill.

[73] Assignee: Pittway Corporation, Chicago, Ill.

[21] Appl. No.: 522,599

[22] Filed: Sep. 1, 1995

[51] Int. Cl.$^6$ ............................................. G08B 29/00
[52] U.S. Cl. ..................... 340/511; 340/501; 340/518; 340/825.06
[58] Field of Search ................... 340/511, 519, 340/517, 506, 501, 825.06, 825.09

[56] References Cited

U.S. PATENT DOCUMENTS

| | | | |
|---|---|---|---|
| 4,524,382 | 6/1985 | Tanaka et al. | 358/31 |
| 4,916,432 | 4/1990 | Tice et al. | 340/518 |
| 5,084,696 | 1/1992 | Guscott et al. | 340/541 |
| 5,119,321 | 6/1992 | Burton, Jr. et al. | 364/574 |
| 5,372,029 | 12/1994 | Brandes | 340/511 |
| 5,471,194 | 11/1995 | Guscott | 340/511 |

OTHER PUBLICATIONS

European Search Report—Application No. EP 96 30 6322.
I.E.E.E. Transactions on Instrumentation & Measurement—vol. IM-36, No. 3, Sep. 1987, NY, USA, p. 851—Rathore et al. "Digital Maximum/Minimum Indicator".

*Primary Examiner*—Jeffery Hofsass
*Assistant Examiner*—Daryl C. Pope
*Attorney, Agent, or Firm*—Dressler, Rockey, Milnamow & Katz, Ltd.

[57] ABSTRACT

An apparatus and a method can be used to pre-process an output signal from an ambient condition sensor. The pre-processing removes noise pulses which are not correlated with an ambient condition being sensed. Preprocessing can be carried out by comparing the present output value to a prior output value and selecting a minimum value there between. The apparatus and method can incorporate storage for two prior values and the present output value can be compared to two prior values and a minimum or a maximum of the three values selected. Additional processing can be carried out by comparing the present output value to a nominal expected clear air output value. If the present value exceeds the nominal expected output value, a minimum is selected among the present output value and one or more prior values. If the present output value is less than the nominally expected value, a maximum is selected from among the present output value and one or more prior output values.

20 Claims, 8 Drawing Sheets

PRE-PROCESSOR APPARATUS AND METHOD

FIELD OF THE INVENTION

The invention pertains to the suppression of random noise on electrical signals received from ambient condition sensors. More particularly, the invention pertains to processing apparatus and methods for minimizing random noise variations in electrical signals indicative of ambient conditions such as smoke or fire.

BACKGROUND OF THE INVENTION

Various systems are known for the detection of alarm conditions. One particular form of such a system is a smoke or fire detecting system of a type generally illustrated in previously issued Tice et al. U.S. Pat. No. 4,916,432, assigned to a common assignee and incorporated herein by reference.

Upon receipt of inputs from one or more of the detectors of the system, a control unit associated with the system is able to make a determination as to whether or not a fire condition is present in one or more reasons of interest. A variety of techniques have been used in the past for the purpose of making this determination.

Sensors of smoke such as photoelectric smoke detectors or ionization-type smoke detectors are intended to provide outputs indicative of sensed levels of ambient smoke. Environmental noise, such as dust particles or insects which may enter the respective detector can produce variations in output signals from the sensors which are not in any way correlated with the presence of smoke. These noise outputs can produce false alarms if the sensitivity of the respective detector is high enough. Such false alarms are undesirable.

Prior attempts at addressing this problem have been successful only in part. Screens have been used in detectors to block the entry of insects into the unit. The sensitivity of a given detector can be reduced thereby requiting larger output signals to produce a false alarm condition, (also larger output signals to produce a true alarm condition). This is a less than desirable solution since it will delay the generation of an alarm signal in the presence of smoke or fire. Alternately, some form of filtering or smoothing of the output signal, either analog or digital, can be used for purposes of reducing the effects of such random transient noise.

Nevertheless, there continues to be a need for improved apparatus and techniques for minimizing the effects of random noise so that detectors can be operated with the highest possible sensitivity yet still be sufficiently immune from false alarming due to noise transients. Preferably, such apparatus and methods could be incorporated into detectors without significantly increasing the complexity or the expense thereof.

SUMMARY OF THE INVENTION

An apparatus to pre-process an output signal from an ambient condition sensor can be located at or remote from the sensor. The preprocessing apparatus removes noise pulses which are not correlated with an ambient condition being sensed.

Preprocessing can be carried out by comparing the present output value from the sensor to a prior output value and selecting a minimum value therebetween. The apparatus can incorporate storage for two prior values and the present output value can be compared to two prior values and a minimum of the three values selected.

Additional processing can be carried out by comparing the present output value to a nominal expected output value. If the present value exceeds the nominal expected output value, a minimum is selected among the present output value and one or more prior values. If the present output value is less than the nominally expected value, a maximum is selected from among the present output value and one or more prior output values.

A processing method in accordance with the present invention includes the steps of:

(a) establishing a measurement interval;

detecting a current value of an ambient condition and generating a signal indicative thereof;

(c) comparing current value of the signal to at least one prior value of the signal;

(d) selecting a minimum value as an output value as a result of the comparing step;

(e) storing the current signal value; and (f) executing steps (b)–(e) during the next measurement interval.

Numerous other advantages and features of the present invention will become readily apparent from the following detailed description of the invention and the embodiments thereof from the claims and from the accompanying drawings.

DETAILED DESCRIPTION OF THE PREFERRED EMBODIMENT

Figure 1:
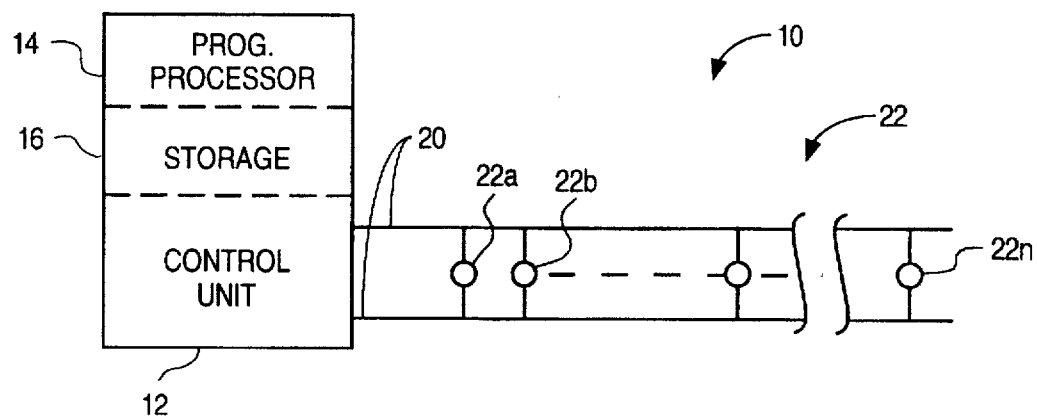
FIG. 1 is a block diagram of an alarm system in accordance with the present invention.

While this invention is susceptible of embodiment in many different forms, there are shown in the drawing, and will be described herein in detail, specific embodiments thereof with the understanding that the present disclosure is to be considered as an exemplification of the principles of the invention and is not intended to limit the invention to the specific embodiments illustrated.

FIG. 1 illustrates a block diagram of a system 10 in accordance with the present invention. This system 10 includes a control unit 12, which can be implemented with a programmable processor 14 and a storage unit 16. The storage unit 16, which can be implemented using read-only storage, read/write storage or electrically programmable read-only storage, can include both control programs and data storage regions for use by the processor 14.

The control unit 12 is coupled by a bidirectional communication link 20 to a plurality of ambient condition sensors or detectors generally indicated at 22. The members of the plurality 22, such as sensors 22a, 22b–22n are intended to detect a particular ambient condition in an adjacent region.

Representative types of detectors include ionization-type or photoelectric-type smoke detectors. Temperature sensors as well as other types of ambient condition sensors could be used in the system 10 in accordance with the present invention.

Figure 2:
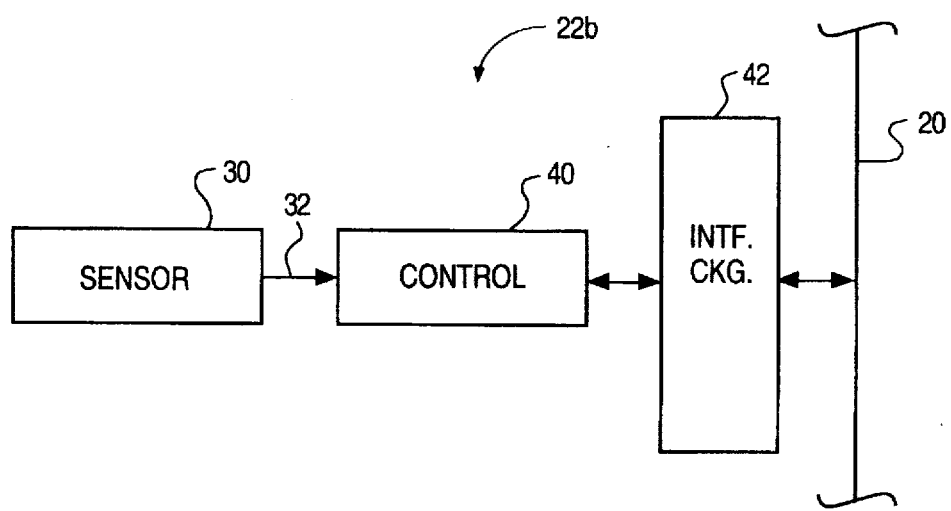
FIG. 2 is a block diagram of a detector usable with the alarm system of FIG. 1.

FIG. 2 is a block diagram representation of a detector 22i useable with the system 10. The detector 22i, includes a sensor element 30. The element 30 is intended to sense a particular ambient condition, such as smoke, temperature, infrared radiation or the like and it generates an electrical system indicative thereof on a line 32.

Figure 3:
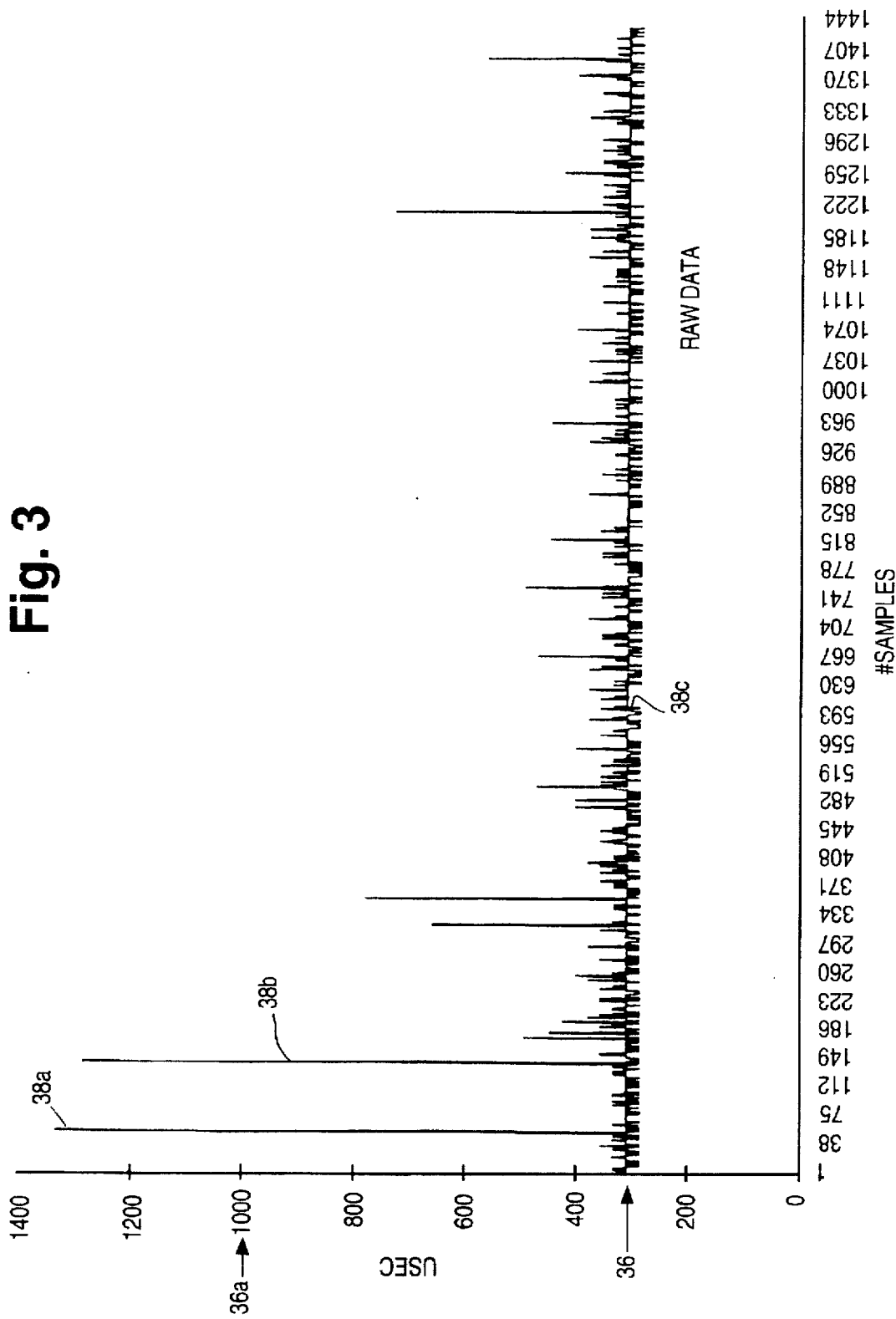
FIG. 3 is a graph of the output of a detector, such as the detector of FIG. 2, as a function of time or sample number in the absence of an ambient condition to be sensed.

FIG. 3 is a graph illustrating output on the line 32 plotted as a function of time or sample number for the sensor 30. In a quiescent or non-alarm condition, as is illustrated in FIG. 3, the sensor 30 generates, on the line 32, a nominal value indicated at 36 in the absence of any selected ambient condition to be detected.

For example, if the sensor 30 was a photoelectric or ionization type sensor, the nominal value 36 would correspond to a clear air output from the sensor 30 indicating an absence of smoke. Similar comments would apply to outputs from representative sensors such as radiant energy sensors, temperature sensors, or other types of ambient condition sensors without limitation.

As is also illustrated on FIG. 3, the sensor 30 produces on the line 32 random noise, indicated by pulses such as pulses 38a, 38b, and 38c. These pulses which in FIG. 3 are not correlated with any ambient condition to be sensed, such as smoke, fire or temperature, represent the presence of random noise conditions to which the sensor 30 responds.

Typical sources of such noise include dust, insects, transient electrical conditions to which the sensor 30 might respond and the like. The pulses 38a–38c, being uncorrelated with any ambient condition to be detected, such as smoke, heat or fire, represent undesirable variations which if unaddressed, could conceivably create false alarming in high sensitivity systems.

Referring again to FIG. 2, output from the sensor 30, on the line 32 is coupled to a local detector control element 40. The control element 40 could be implemented with either digital or analog circuitry. If in digital form, the control element 40 could be implemented as either hard wired logic or could incorporate a programmed microprocessor. The control element 40, via interface circuitry 42 is capable of carrying on bidirectional communication with the system control unit 12, via the communication link 20.

A method in accordance with the present invention, to be described subsequently, could be implemented in either the system control unit 12 or the detector local control element 40 without limitation. Implementation can be by either hard wired circuitry or by means of a programmed microprocessor also without limitation.

Figure 4:
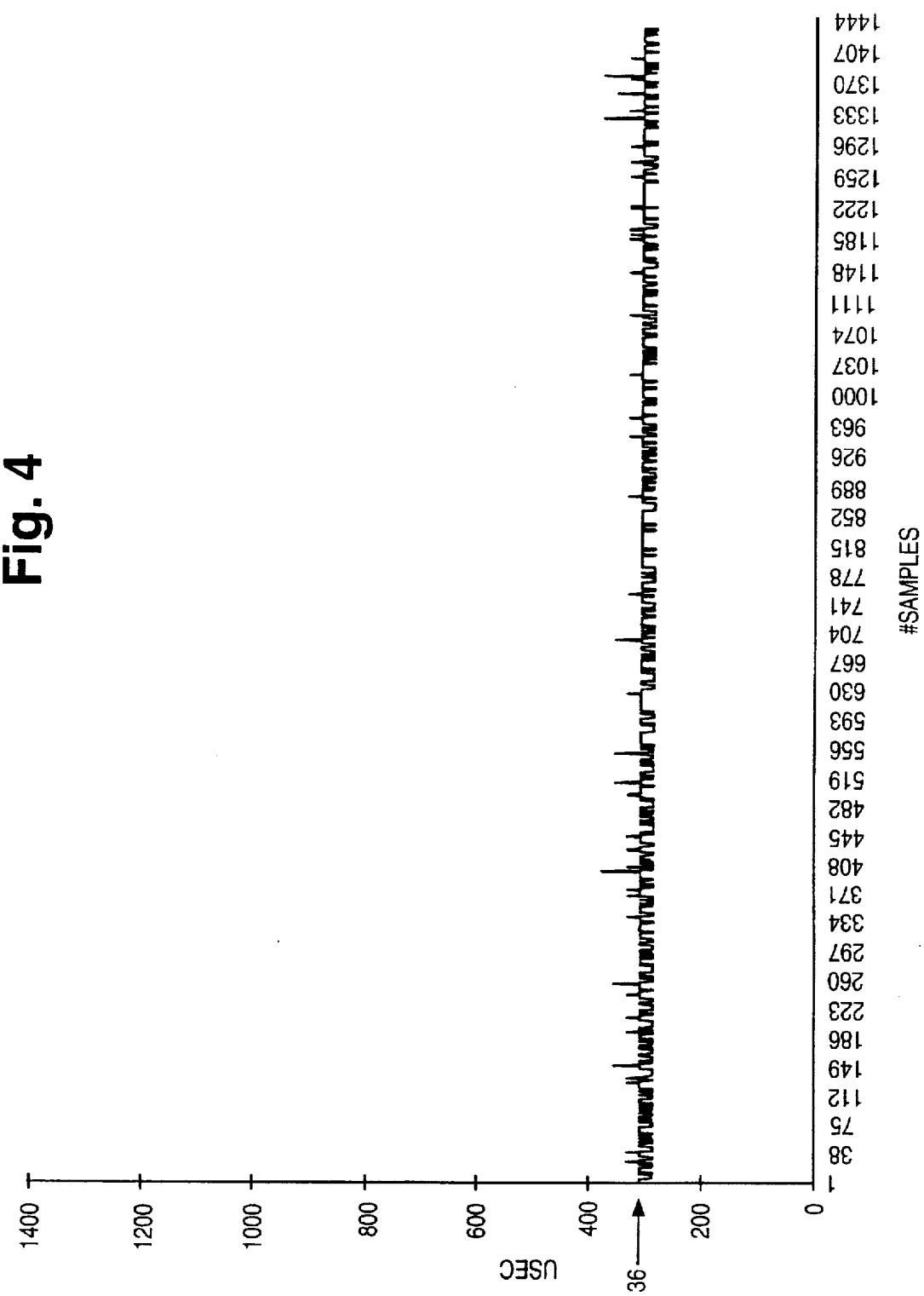
FIG. 4 is a graph of a pre-processed representation of the output sensor signal illustrated in FIG. 3.

FIG. 4 is a graph illustrating the benefits of preprocessing the output of sensor 30, as illustrated in FIG. 3, in accordance with the present invention. The preprocessing illustrated in FIG. 4 can be carried out in either the local control element 40 or the system control unit 12. As illustrated by FIG. 4, the individual noise pulses such as 38a, 38b have been almost completely eliminated.

In accordance with the preprocessing method illustrated in FIG. 4, the present sensor output, on the line 32, is compared to the previous sensor output, from a prior sample time. The minimum of the two values is selected as the present output value. In the event that the present sensor output value exceeds the minimum of the two values, it is replaced in the pre-processed output stream with the minimum value. Hence, a single noise pulse such as the pulse 38a or 38b (FIG. 3) will be completely removed by preprocessing in accordance with the present invention.

The present preprocessing method (FIG. 4) can be represented by the following:

if $output_{N-1}$ is greater than $output_N$ then, set $output_N$=to $output_N$, else $output_N$=$output_{N-1}$.

Thus, using the above preprocessing method, the noise will be substantially removed. However, the response to smoke, heat or fire condition will not be significantly reduced. This response will be delayed but only on the order of one to two sample intervals. This delay can be more than offset in that the sensitivity of each of the detectors for the system 10 can significantly increased due to the removal of the transient noise conditions by use of the present preprocessing method. As such, the system 10 should respond to a fire condition faster, since it can operate with detectors set at a higher sensitivity than would be the case where the sensitivity of the detectors had to be reduced to minimize false alarm problems caused by transient noise.

The preprocessing method illustrated in FIG. 4 can be enhanced by first, selecting the minimum value between the present value and the previous value, assuming the present value exceeds the nominal value 36 which would be expected in the absence of the ambient condition being sensed and in the absence of noise. In addition, selecting the maximum value between the present sensor value and the previous sensor value in the event that the present sensor value is less than the nominal, noise free output 36 will minimize negative going noise sensors. The above steps will eliminate both positive going and negative going noise pulses.

Figure 5:
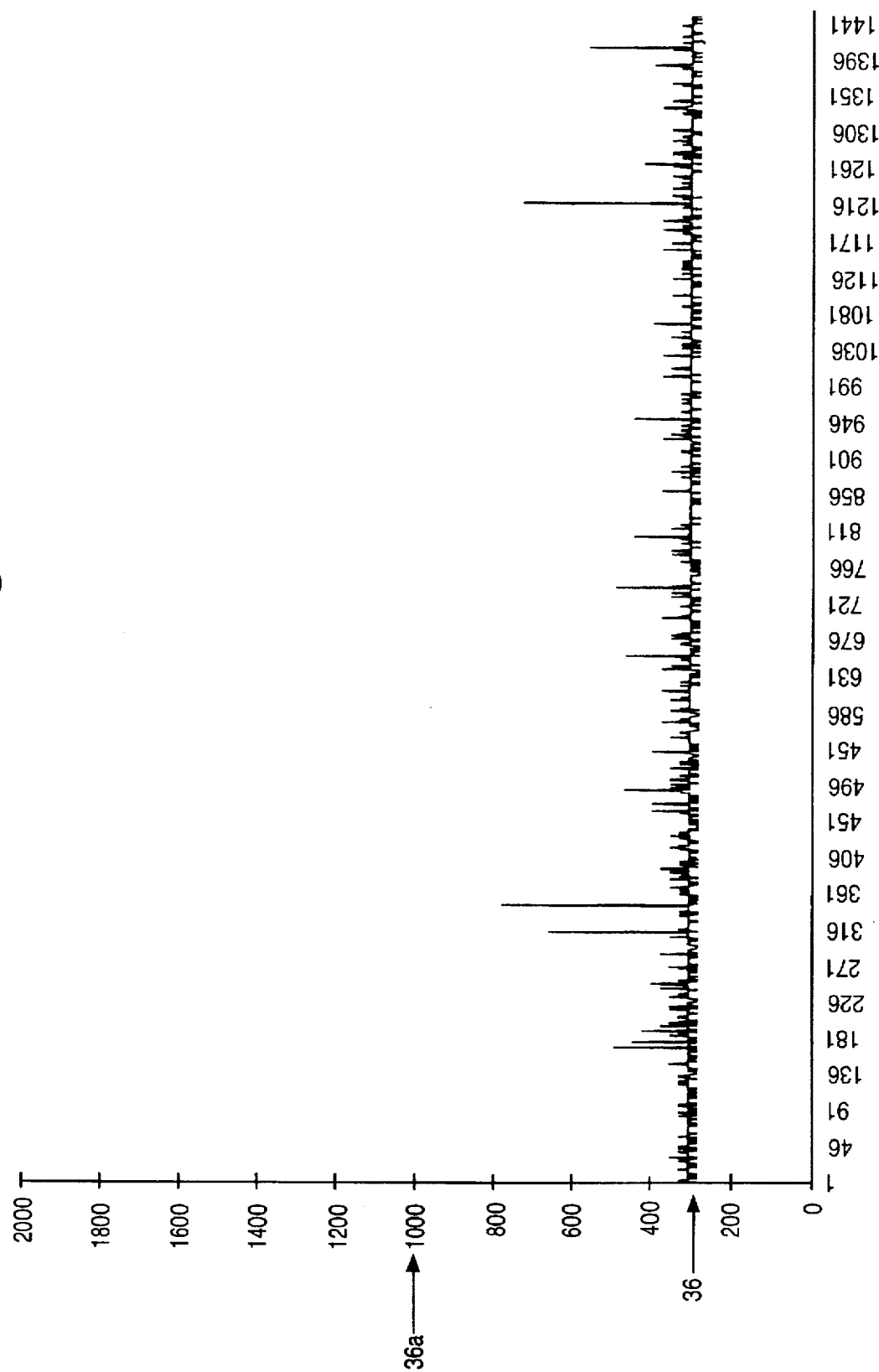
FIG. 5 is a graph of an alternate pre-processed representation of the sensor output signal of FIG. 3.

FIG. 5 is a graph of pre-processed output from the sensor 30 (FIG. 3) processed in accordance with an alternate method. In the method illustrated in FIG. 5, a threshold value, 36a, is set which is in excess of the nominally expected, clear air, output value 36.

In accordance with the method of FIG. 5, the present output value on the line 32, will be compared to the threshold 36a. In the event that the present output value, such as the value 38a, (FIG. 3), exceeds the threshold 36a, the previous output value will be substituted for the present value, 38a, unless the previous value also exceeded the threshold 36a. In this instance, the preprocessor will output, as the present value, the previous value if it is below the threshold 36a (a condition where there are not two consecutive values above that threshold).

A single pulse, such as the pulse 38a will thus be removed only if its amplitude exceeds the threshold 36a as illustrated in FIG. 5. Similar comments apply to the output noise pulse 38b. In accordance with this alternate form of preprocessing, all values below the threshold 36a are output without alteration, for further processing.

Figure 6:
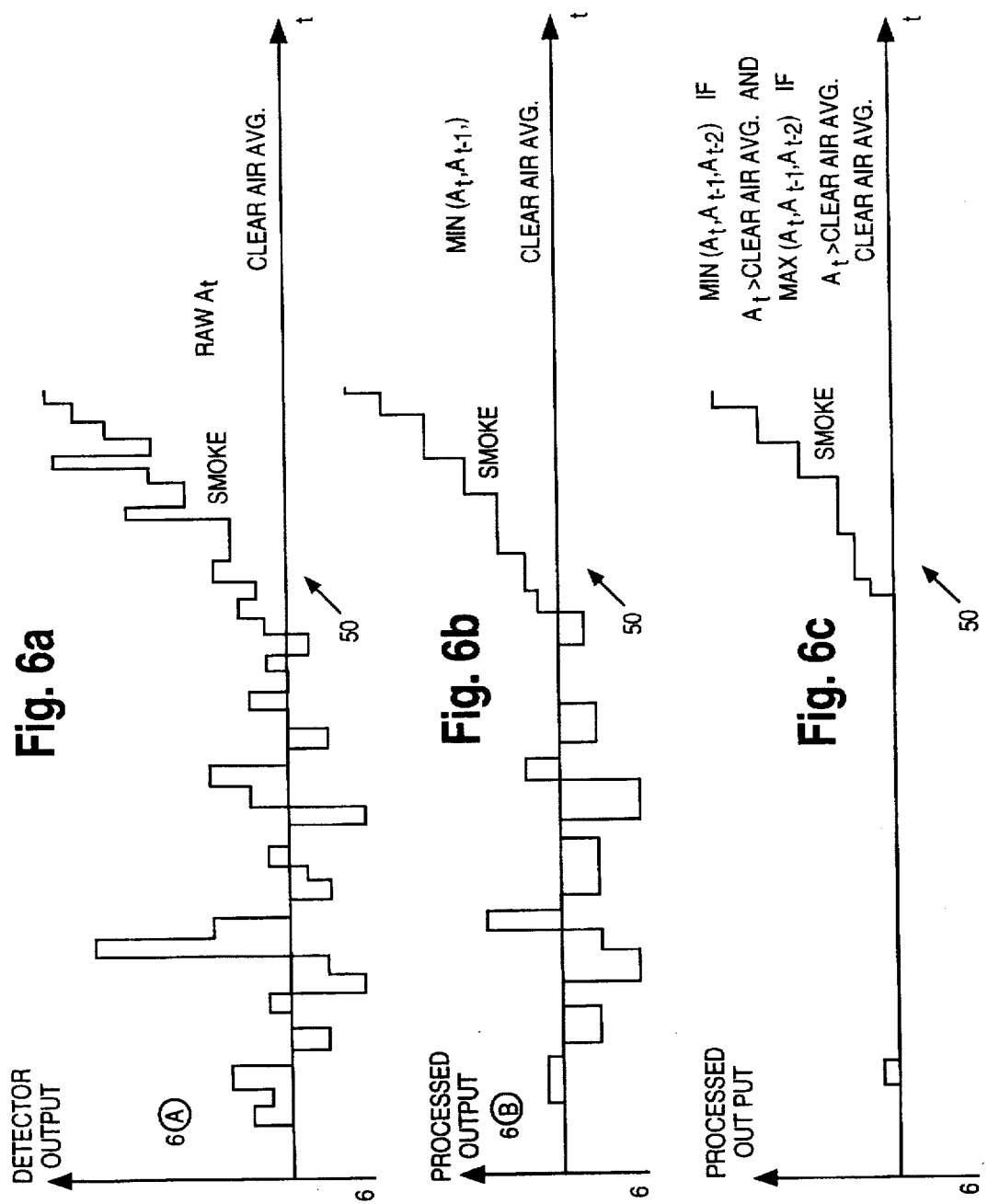
FIGS. 6a–6c are a set of graphs illustrating sensor signal output as well as pre-processed variations thereof.

Other variations are possible without departing from the spirit and scope of the present method. For example, graphs 6A, 6B and 6C illustrate pre-processing using one or two prior output values from the sensor 30. FIG. 6A illustrates schematically sample values from the sensor 30 on the line 32 as a function of sample number or interval as those values vary about the nominal output value 36. In the region 50, the level of sensed smoke is increasing in a non-random fashion in response to smoke being sensed.

FIG. 6B illustrates preprocessing of the signal of FIG. 6A where a minimum of the present output value and one prior output value is selected. As illustrated in FIG. 6B in the presence of smoke, illustrated in region 50, the present pre-processed method provides a smoothed output indicative of the smoke to be detected.

In accordance with another aspect of the method, the present output value from the sensor 30 can be compared to two previously sensed and stored output values. If the present output value exceeds the threshold 36, a minimum value is determined among the present output value, as well as two prior sample values. The minimum is then substituted, in the pre-processed output stream, for the present output value. In the event that either of the prior samples have values below the nominal output threshold 36, they will be treated as if their value was zero.

If the present output value from the sensor 30 is below the nominal output value 36, the present value will be compared to two prior values and the maximum of the three values will be taken as the present output value. In the event that either of the prior output values is equal to or greater than the nominal output threshold 36, that value(s) will be set to zero. Use of two prior values significantly reduced the noise over the use of a single prior value as in FIG. 6B.

FIG. 6C illustrates a pre-processed representation of the signal of FIG. 6A wherein a minimum of the present output value, as well as two prior output values is selected (where the present output value exceeds the nominal output threshold 36). Alternately a maximum of the present output value and two prior output values is selected (where the present output value falls below the nominal output threshold 36). As is illustrated in FIG. 6C, the random uncorrelated noise variations of FIG. 6A have been substantially reduced to zero without providing any significant delay in the pre-processed output in a time interval 50 where smoke is present. More than two prior values can be used if desired.

It will be understood that the exact sample interval is not a limitation of the present invention. Those of skill in the art will understand that an appropriately high sample interval should be chosen, in view of the types of sensors involved as well as the expected rates of change of ambient condition. For exemplary purposes only, and without limitation, sample intervals on the order of five to six seconds appear to be sufficiently short where smoke, heat or fire conditions are being sensed.

Figure 7:
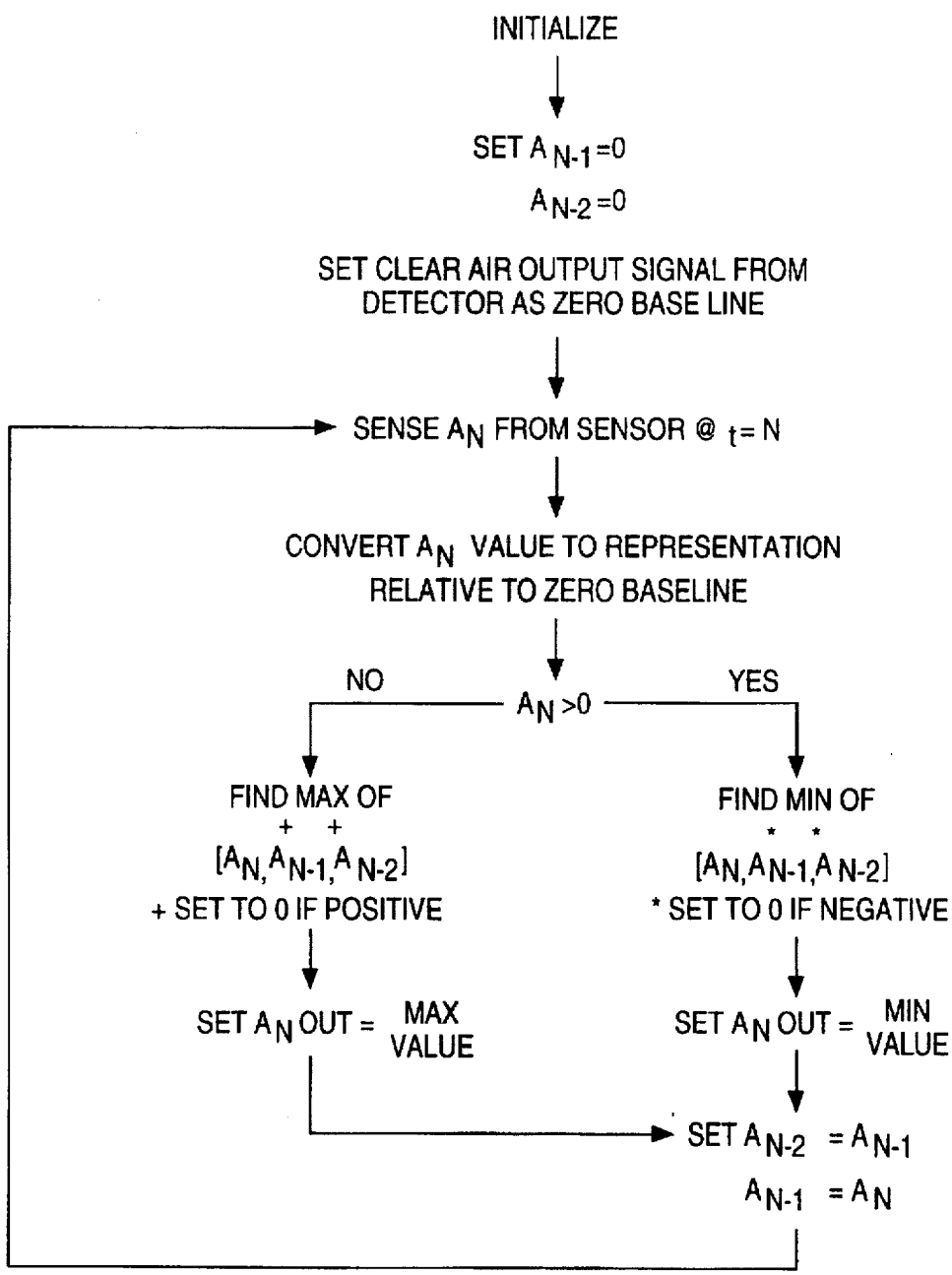
FIG. 7 is a flow diagram illustrating the method of FIG. 6c.

FIG. 7 illustrates a flow diagram of a method in accordance with the processing illustrated in FIG. 6c.

As noted previously, the present method can be implemented at the system control unit 12 on a detector-by-detector basis. Preferably, however it will be implemented directly at the detector 22i. In this instance, the pre-processed output will be transmitted by the communication link 20 to the control unit 12 for further processing and analysis.

Figure 8:
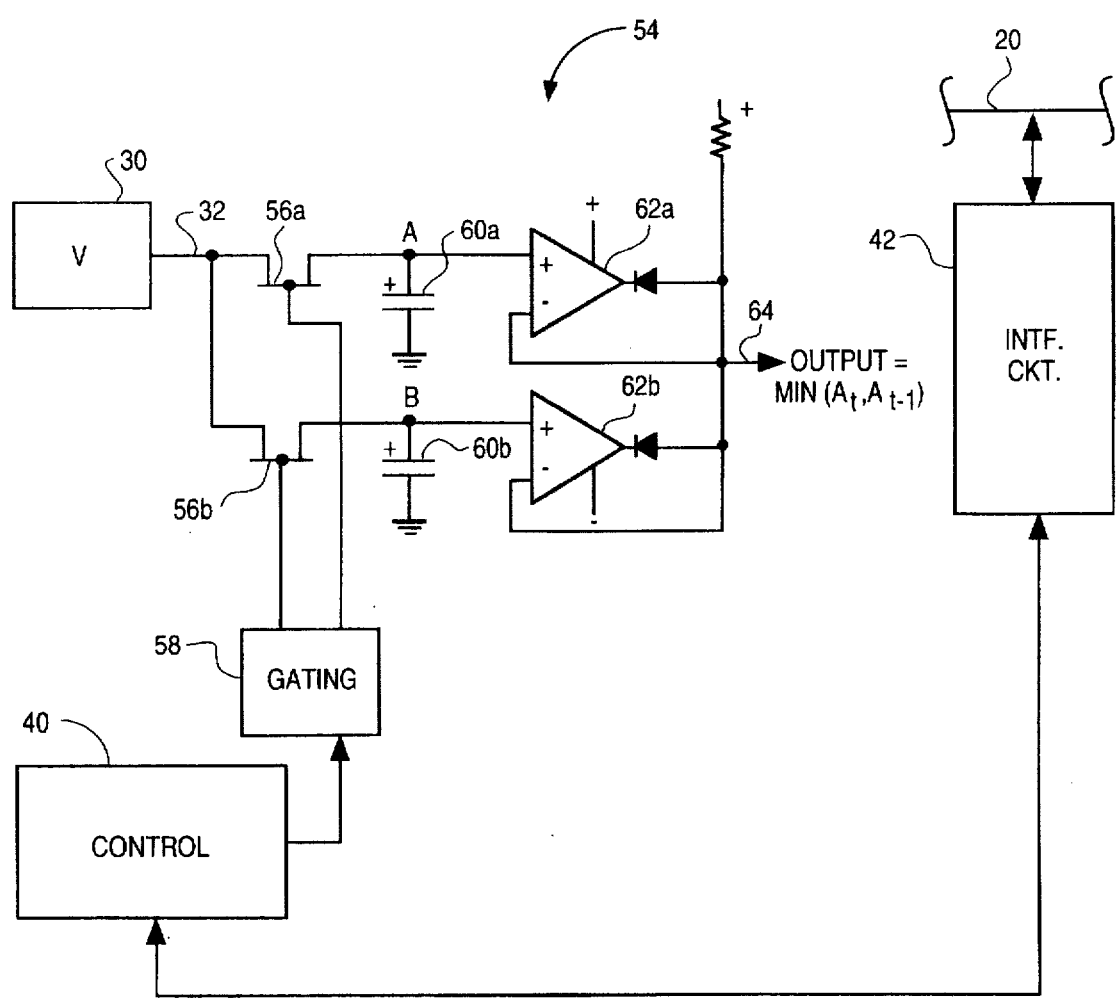
FIG. 8 is a block diagram schematic of an analog pre-processing circuit.

FIG. 8 is a schematic of a circuit 54 usable to implement the method of FIG. 4. As illustrated in FIG. 8, preprocessing circuitry 54, which could be incorporated into the local control element 40, receives an analog voltage on the line 32 from the sensor 30. First and second solid state switches 56a and 56b receive the varying output voltage on the line 32. Gating 58, which could be coupled to hard wired control logic in the control element 40 or could be coupled to a programmable microprocessor therein, provides alternating gate input signals to the gates of the switches 56a, 56b.

When one of the switches 56a, 56b is caused to conduct, the analog voltage on the line 32 is stored on a respective capacitor 60a or 60b. The capacitors 60a, 60b provide inputs to operational amplifiers 62a, 62b. An output on a line 64 represents the minimum of the present analog value on the line 32 and the previous sampled analog value on the line 32.

The control element 40 can then forward the minimum value on the line 64, via communications link 20 to the system control unit 12. It will also be understood that the preprocessing circuitry 54 could incorporate detection to determine whether or not the present value $A_N$ is greater than or less than the nominal output value 36 and/or is above or below the threshold value 36a.

Figure 9:
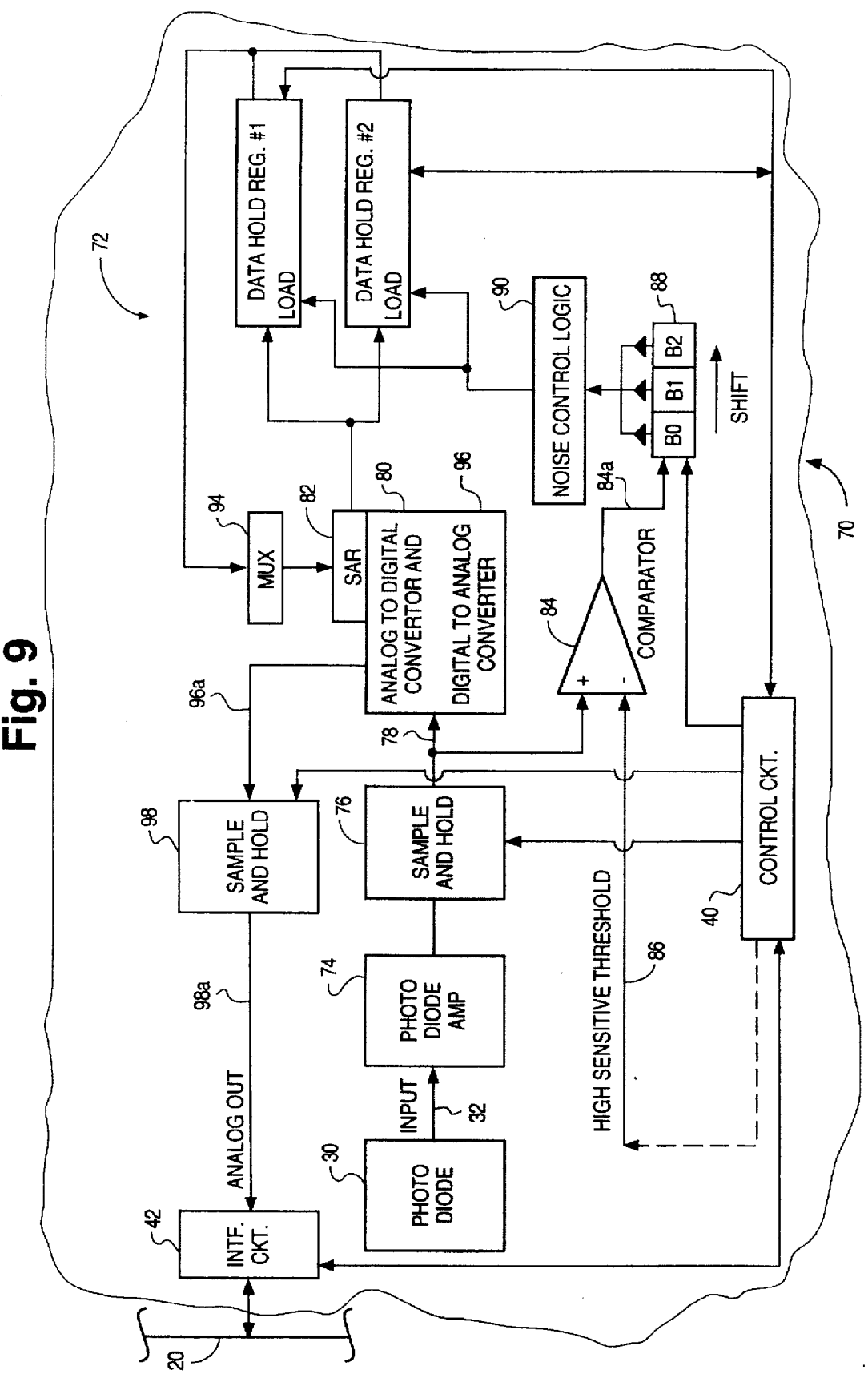
FIG. 9 is a block diagram schematic of a digital preprocessing circuit.

Preprocessing can also be carried out locally in the local control unit 40 using digital techniques as illustrated in the schematic of FIG. 9.

FIG. 9 illustrates a detector 70 which incorporates a digital preprocessing circuit indicated generally at 72. The detector 70 includes the sensor 30 which could for example be a photoelectric sensor with an output which varies as a function of time on the line 32. The detector 70 also includes control circuitry 40 which could be a hard wire or implemented as a programmed microprocessor.

Output signals from the photo sensor, on the line 32 are amplified in an amplifier 74 and sampled and held in a sample and hold circuit 76. The sample and hold circuit 76 operates under the control of the control circuit 40.

The analog output from the sample and hold circuit 76, on the line 78 is digitized by an analog-to-digital converter 80. The digitized representation of the analog signal on the line 78 is temporarily stored in SAR register 82.

In addition to converting the analog signal to a digital representation in the analog-to-digital converter 80, the analog value is compared in a comparator 84 to a prestored high sensitivity threshold on a line 86. The value of that prestored high sensitivity threshold can be programmable under control of the control circuitry 40 or it can be pre-established using a voltage divider formed of resisters.

Output from the comparator 84, on a line 84a, indicates whether or not the present analog value is greater than or less than the high sensitivity threshold on the line 86. The results of the current comparisons are loaded into a three-bit shift register 88. The shift register 88, which shifts the contents thereof under the control of the control circuit 40 stores the results of the present comparison as well as the results of the two prior comparisons.

The outputs from the shift register 88 feed noise control combinational logic 90. The noise control logic 90 analyzes the contents of the shift register 88 and in response thereto may load the digitized contents of the SAR register 82 into the data hold registers R1, R2.

The outputs of register R1, R2 are fed to a multiplexer 94. The multiplexer 94, which operates under the control of control circuitry 40, can select the contents of one of the two registers R1, R2, which selected contents can then be converted in a digital-to-analog converter 96 to an analog value.

The analog value, output on the line 96a, is fed to a sample and hold amplifier 98. The sample and hold amplifier 98 produces a preprocessed, sampled, analog output value on line 98a. The analog output value on the 98a can be coupled by the interface circuitry 42 and communication link 20 to the system control unit 12.

The noise control logic 90 will always enable loading of the contents of the SAR register 82 into the registers R1, R2 when the current analog value, on the line 78 is less than the high sensitivity threshold set on the line 86. In this instance, the contents of the SAR register 82 are gated into registers R1, R2 and via multiplexer 94 and digital to analog converter 96 presented to sample and hold amplifier 98.

The output of sample and hold amplifier 98 becomes a pre-processed representation of the analog input signal on the line 32. If the sample voltage on the line 78 is greater than the high sensitivity threshold on the line 86, the current value and the SAR register 82 will not be gated into the registers R1, R2. Instead, the content of one of the registers R1, R2 a digitized representation of the prior analog value is gated by multiplexer 94 and digital-to-analog converter 96 to the sample and hold amplifier 98 for output. This analog value on the line 98a, corresponding to the previously sampled analog value, thus becomes the present pre-processed analog output value.

In the event that the bits B0, B1 of shift register 88 indicate that the present analog value, and the previous analog value both exceeded the high sensitivity threshold on the line 86, then the contents of the SAR register 82 (the digitized representation of the current sampled analog value) will be gated into one of registers R1, R2 and those contents through multiplexer 94 and digital-to-analog converter 96 will be presented in analog form to the sample and hold amplifier 98 as a pre-processed analog output value.

In the above described implementation, the first analog value which exceeds the high sensitivity threshold on the line 96 is disregarded in the preprocessing and the previous sensor analog value output to the interface circuitry 42. However, if a second immediately following analog value exceeds the high sensitivity threshold, an analog representation of the present analog value on the line 32 will be output to the interface circuitry 42 despite the fact that it exceeds the high sensitivity threshold on the line 86.

If desired, where the control circuitry 40 incorporates a microprocessor, additional processing can be carried out on the contents of registers R1 and R2 without departing from the spirit and scope of the present invention.

In an alternate embodiment, the preprocessing circuitry 72 can carry out preprocessing of ambient condition values in accordance with the graph of FIG. 6c and flow diagram of FIG. 7. In response to such preprocessing, control circuit 40 can output to the communications link 20, via interface circuitry 42, a maximum of the present value and one or more prior values (where the present value is below a dear air or preset threshold), or, a minimum of the present value and one or more prior values (where the present value is above a clear air or preset threshold.)

From the foregoing, it will be observed that numerous variations and modifications may be effected without departing from the spirit and scope of the invention. It is to be understood that no limitation with respect to the specific apparatus illustrated herein in tended or should be inferred. It is, of course, intended to cover by the appended claims all such modifications as fall within the scope of the claims.

We claim:

1. A method of processing a time varying signal indicative of an ambient condition comprising the steps of:
   (a) establishing a measurement interval;
   (b) detecting a current value of an ambient condition and generating a signal indicative thereof;
   (c) comparing the current value of the signal to at least one prior value of the signal;
   (d) selecting one of a minimum value or a maximum value, the values having different magnitudes, as an output value as a result of the comparing step;
   (e) storing the current value of the signal; and
   (f) executing steps (b)–(e) during the next measurement interval.

2. The method as in claim 1 wherein the current value of the signal is compared to a predetermined threshold and wherein in step (d) the minimum value is selected in response to the current value of the signal exceeding the threshold.

3. The method as in claim 1 wherein the current value of the signal is compared to a predetermined threshold and wherein in step (d) the maximum value is selected in response to the current value of the signal not exceeding the threshold.

4. The method as in claim 1 wherein the at least two prior signal values are stored in digital form.

5. A method of processing a time varying signal indicative of an ambient condition comprising the steps of:
   (a) establishing a measurement interval;
   (b) detecting a current value of an ambient condition and generating a signal indicative thereof;
   (c) comparing a detected current value of the signal to a predetermined threshold, and, in response to the current value of the signal being less than the threshold:
      comparing the current value of the signal to at least one prior value;
      selecting a maximum value as an output value as a result of the comparing step;
   (d) storing the current value of the signal; and
   executing steps (b)–(e) during the next measurement interval.

6. A pre-processing circuit for reducing noise variations in an electrical signal comprising:
   circuitry for detecting a current value of an electrical signal;
   circuitry for storing at least one prior, sampled, value of the electrical signal;
   circuitry for comparing said stored, prior, sampled, signal value to at least said current value of the electrical signal;
   circuitry for selecting one of a minimum or a maximum of said two compared signal values, the values having different magnitudes as an output value; and
   circuitry for storing said current value of the electrical signal.

7. The pre-processing circuit as in claim 6 which includes:
   circuitry for establishing at least one threshold value.

8. A pre-processing circuit for reducing noise variations in an electrical signal comprising:
   circuitry for detecting a current value of an electrical signal;
   circuitry for storing at least one prior, sampled, value of the electrical signal;
   comparison circuitry for comparing said stored, prior, sampled, signal value to said current value of the electrical signal;
   circuitry for selecting one of a minimum or a maximum of said two compared signal values;
   circuitry for storing said current value of the electrical signal;
   circuitry for determining if the current value of the electrical signal is above a nominal value; and
   wherein said circuitry for selecting a minimum is enabled when said current value of the electrical signal is above said nominal value and wherein said circuitry for selecting a maximum is enabled where said circuit value of the electrical signal is below said nominal value.

9. A detector with a pre-processing circuit comprising:

an ambient condition sensor wherein said sensor generates output values indicative of the ambient condition; and pre-processing circuitry coupled to said sensor wherein said circuitry includes:

a control element;

a storage element, coupled to said control element wherein at least one of said values is stored in said element; and wherein said control element detects values from said sensor and compares a current value to at least one prior value and wherein said control element includes circuitry for selecting one of said at least two values, the values having different magnitudes, in accordance with a predetermined criterion, wherein said selected value is output from said pre-processing circuit as a pre-processed representation of the current value and wherein said current value is stored in said storage element.

10. The detector as in claim 9 which includes circuitry for establishing a sample interval wherein said output values from said sensor are sampled at least once each sample interval.

11. The detector as in claim 9 wherein said control element includes circuitry for selecting a maximum of said at least two compared values.

12. The detector as in claim 9 wherein said control element includes circuitry for selecting a minimum of said at least two compared values.

13. The detector as in claim 9 wherein said storage element includes circuitry for storage of analog values.

14. The detector as in claim 9 wherein said control element includes a microprocessor.

15. A method of processing a time varying signal indicative of an ambient condition comprising the steps of:

(a) establishing a measurement interval;

(b) detecting a current value of an ambient condition and generating a signal indicative thereof;

(c) comparing the current value of the signal to at least two prior stored values of the signal;

(d) selecting one of a minimum value or a maximum value of the compared signal values, the values having different magnitudes, as an output value as a result of the comparing step;

(e) storing the current value of the signal; and (f) executing steps (b)–(e) during the next measurement interval.

16. A pre-processing circuit for reducing noise variations in an electrical signal comprising:

circuitry for establishing at least one threshold value;

circuitry for detecting a current value of an electrical signal;

circuitry for storing at least one prior, sampled, value of the electrical signal;

circuitry for comparing said stored, prior, sampled, signal value to at least said current value of the electrical signal;

circuitry for selecting one of a minimum value or a maximum value of said two compared signal values, the values having different magnitudes, as an output value;

circuitry for storing said current value of the electrical signal; and circuitry for enabling the comparison circuitry only when the current value of the electrical signal exceeds the threshold value.

17. The pre-processing circuit as in claim 16 which includes circuitry for establishing a sample interval.

18. A method of processing a time varying signal indicative of an ambient condition comprising the steps of:

generating a first signal representing an ambient condition;

storing the first signal;

generating a second signal representing an ambient condition;

comparing the first signal to the second signal;

generating a third signal representative of an ambient condition; and comparing the third signal to the first and second signals; and generating an output in response to the comparison wherein the output equals one of the maximum value of the first, second, third signals or the minimum value of the first, second, third signals wherein the values are different.

19. A method of processing a time varying signal indicative of an ambient condition to produce an output that corresponds to a prior or present signal value, the method comprising the steps of:

(a) establishing a measurement interval;

(b) detecting a present value of an ambient condition signal;

(c) comparing the present value of the signal to a least one prior stored value of the signal;

(d) selecting one of a minimum value or a maximum value of the compared signals, the values having different magnitudes, as the output value of the comparing step;

(e) and storing the present value of the signal which may be used as a prior stored value in the next comparison.

20. A pre-processing circuit comprising:

circuitry for detecting a current value of an electrical signal;

circuitry for forming a current representation of the signal;

circuitry for storing at least one, prior representation of the signal;

circuitry for comparing at least the stored prior representation of the signal to at least the current representation;

circuitry for selecting one of the two compared representations; wherein the representations have different magnitudes, in accordance with a predetermined criterion; and circuitry for storing the current representation.

* * * * *